US012059293B2

(12) United States Patent
Løype

(10) Patent No.: US 12,059,293 B2
(45) Date of Patent: Aug. 13, 2024

(54) MOTION CONTROL LOCKING MECHANISM FOR INTERVENTIONAL IMAGING PROBE

(71) Applicant: GE Precision Healthcare LLC, Wauwatosa, WI (US)

(72) Inventor: Birger Løype, Horten (NO)

(73) Assignee: GE Precision Healthcare LLC, Wauwatosa, WI (US)

( * ) Notice: Subject to any disclaimer, the term of this patent is extended or adjusted under 35 U.S.C. 154(b) by 6 days.

(21) Appl. No.: 17/680,689

(22) Filed: Feb. 25, 2022

(65) Prior Publication Data

US 2023/0270406 A1 Aug. 31, 2023

(51) Int. Cl.
*A61B 8/00* (2006.01)
*A61B 8/02* (2006.01)
*A61B 8/12* (2006.01)

(52) U.S. Cl.
CPC .......... *A61B 8/42* (2013.01); *A61B 8/02* (2013.01); *A61B 8/12* (2013.01); *A61B 8/4444* (2013.01); *A61B 8/54* (2013.01)

(58) Field of Classification Search
CPC .... A61B 8/42; A61B 8/02; A61B 8/12; A61B 8/4444; A61B 8/54
See application file for complete search history.

(56) References Cited

U.S. PATENT DOCUMENTS

| 5,445,154 | A | * | 8/1995 | Larson | A61B 8/445 600/459 |
| 5,467,779 | A | * | 11/1995 | Smith | A61B 8/4245 600/463 |
| 2009/0105798 | A1 | * | 4/2009 | Koch | A61F 2/95 623/1.11 |
| 2011/0166455 | A1 | * | 7/2011 | Cully | A61B 8/4245 600/463 |
| 2021/0220001 | A1 | * | 7/2021 | Heiliger | A61B 34/37 |

OTHER PUBLICATIONS

Aaron Black (Worm Gears Explained; Machinery Lubrication; Published by Noria; 2021 Noria Corporation) (Year: 2021).*

* cited by examiner

*Primary Examiner* — Alexei Bykhovski
(74) *Attorney, Agent, or Firm* — Boyle Fredrickson S.C.

(57) ABSTRACT

An invasive/interventional device or probe includes a control handle operably connected to an imaging system and an insertion tube. The control handle includes a body, a movement control mechanism disposed at least partially within the body and having one or more control elements disposed on the body, one or more gears rotatably disposed within the body, operably connected to the control elements, and one or more cables engaged with the gears, the cables extending outwardly from the body and adapted to be engaged with a tip of the interventional medical device. The control handle further includes a motion locking mechanism disposed at least partially within the body, the motion locking mechanism having one or more brake rods biased into engagement with the gears and a release switch engaged with the brake rods to selectively position the brake rods into or out of engagement with the gears.

20 Claims, 19 Drawing Sheets

MOTION CONTROL LOCKING MECHANISM FOR INTERVENTIONAL IMAGING PROBE

FIELD AND BACKGROUND OF THE INVENTION

Embodiments of the present disclosure relate generally to interventional imaging and, more particularly, to structures of control handles used for manipulation of the interventional imaging probes and their method of operation in interventional procedures.

Various medical conditions affect internal organs and structures. Efficient diagnosis and treatment of these conditions typically require a physician to directly observe a patient's internal organs and structures. For example, diagnosis of various heart ailments often requires a cardiologist to directly observe affected areas of a patient's heart. Instead of more intrusive surgical techniques, ultrasound imaging is often utilized to directly observe images of a patient's internal organs and structures.

By way of example, interventional procedures such as transesophageal echocardiography (TEE) and/or intracardiac echocardiography (ICE) may be used to provide high resolution images of intracardiac anatomy. The high-resolution images, in turn, allow for real-time guidance of interventional devices during structural heart disease (SHD) interventions such as transcatheter aortic valve implantation (TAVI), paravalvular regurgitation repair, and/or mitral valve interventions.

TEE procedures are typically performed in examination, intervention and operating room (open heart surgery) situations where imaging of internal structures of the patient is required. The device utilized in performing TEE typically includes an invasive or interventional device or probe, a processing unit, and a monitor. The probe is connected to the processing unit which in turn is connected to the monitor. In operation, the processing unit sends a triggering signal to the probe. The probe then emits ultrasonic signals via an imaging element within the probe into the patient's heart. The probe then detects echoes of the previously emitted ultrasonic signals. Then, the probe sends the detected signals to the processing unit which converts the signals into images. The images are then displayed on the monitor. The probe typically includes a semi-flexible insertion tube that includes a transducer located near the end of the probe.

Typically, during TEE, the insertion tube is introduced into the mouth of a patient and positioned in the patient's esophagus. The insertion tube is then positioned so that the transducer is in a position to facilitate heart imaging. That is, the insertion tube is positioned so that the heart or other internal structure to be imaged is in the direction of view of the imaging element or transducer disposed within the insertion tube. Typically, the transducer sends ultrasonic signals through the esophageal wall that come into contact with the heart or other internal structures. The transducer then receives the ultrasonic signals as they bounce back from various points within the internal structures of the patient. The transducer then sends the received signals back through the insertion tube typically via wiring. After the signals travel through the insertion tube and probe, the signals enter the processing unit typically via wires connecting the probe to the processing unit.

Often, in addition to the heart, it may be desirable to image other internal structures within the body of a patient using other interventional imaging procedures and devices, including bronchoscopes or colonoscopes, for example. Imaging other internal structures may require re-positioning or use of a different probe in order to view the internal organs or other internal structures of the patient that are desired. Additionally, viewing the heart and/or other internal structures from various angles and perspectives may require re-positioning of the probe during these procedures.

Although TEE allows for well-defined workflows and good image quality, TEE may not be suitable for all cardiac interventions. Accordingly, in other interventional procedures, ICE may be used to provide high resolution images of cardiac structures, often under conscious sedation of the patient. Furthermore, ICE equipment, which utilizes probes highly similar in construction to those used for TEE, may be interfaced with other interventional imaging systems, thus allowing for supplemental imaging that may provide additional information for device guidance, diagnosis, and/or treatment. For example, a CT, MRI, PET, ultrasound, fluoroscopy, electrophysiology, and/or X-ray imaging system may be used to provide supplemental views of an anatomy of interest in real-time to facilitate ICE-assisted interventional procedures.

In either of these procedures or in any similar invasive or interventional procedure, as previously discussed, as shown in FIGS. 1-3, the probe or interventional device 1000 inserted into the patient 1002 includes a control handle 1004 with an elongate, flexible insertion tube 1006 extending outwardly from the handle 1004. The tube 1006 encloses a suitable movement mechanism 1007 that is operably connected to a control device 1008 on the control handle 1004, such that an operator can control the movement of the mechanism 1007, and the movement of the flexible tube 1006, within the patient 1002. Opposite the control handle 1004, the flexible insertion tube 1006 includes an imaging element, e.g., a transducer 1010, that is operable to obtain the ultrasound images of the anatomy 1018 of the patient 1002.

In certain prior art interventional probe control handle configurations, as shown in FIGS. 1 and 2, the probe 1000 has a control handle 1004 that enables the user to manipulate the transducer 1010 inside an esophagus 1020 of the patient 1002 in two planes, i.e., an anterior—posterior (AP) plane 1014, and a left—right (RL) plane 1016, so that the needed images of the structure of interest in the anatomy 1018, e.g., the heart, can be acquired via the transducer 1010. In order to move the transducer 1010 within either of the planes 1014, 1016, the control device 1008 disposed on the control handle 1004 enables the selective control of the movement of the transducer 1010 in either plane 1014,1016. For example, the control device 1008 can take the form of a pair of control wheels 1022,1024 rotatably mounted to the control handle 1004. By rotating the small control wheel 1022, the transducer 1010 can be manipulated in the RL plane 1016, i.e., either left or right relative to the anatomy 1018 of the patient 1002. By rotating the large control wheel 1024, the transducer 1010 can be manipulated in the AP plane 1014, i.e., either anteriorly or posteriorly relative to the anatomy 1018 of the patient 1002.

While the probe 1000 is in use, to maintain or hold the desired position for the transducer 1010 to obtain a particular image view, the user can actively hold onto the wheels 1022,1024 for shorter periods of time to prevent any inadvertent movement of the wheels 1022,1024 and, consequently the transducer 1010. But if the image view for the transducer 1010 needs to be held for a longer period of time, the user can activate a deflection brake or deflection lock 1026 on the control handle 1004. The deflection lock 1026 secures the wheels 1022,1024 in the selected position and prevents any movement of the wheels 1022,1024 until the lock 1026 is disengaged.

In the prior art, the deflection lock 1026 can have various forms, such as those disclosed in each of U.S. Pat. Nos. 9,999,434; 9,924,855; 9,526,406; 9,259,141; 8,808,168; 10,064,639; and 6,699,182, but each includes one or more deficiencies with regard to the structure and/or mode of operation of the lock. Therefore, is desirable to develop an improved deflection lock for an interventional probe that avoids these shortcomings of the prior art.

BRIEF DESCRIPTION OF THE DISCLOSURE

In one exemplary embodiment of the invention, a control handle for an interventional medical device includes a body, a movement control mechanism disposed at least partially within the body, the movement control mechanism having one or more control elements disposed on the body, one or more gears rotatably disposed within the body and operably connected to the one or more control elements. The one or more gears including a number of engagement structures thereon and one or more cables engaged with the one or more gears, the one or more cables extending outwardly from the body and adapted to be engaged with a tip of an interventional medical device, and a motion locking mechanism disposed at least partially within the body, the motion locking mechanism having one or more brake rods biased into engagement with the engagement structures on the one or more gears and a release switch engaged with the one or more brake rods to selectively position the one or more brake rods into or out of engagement with the engagement structures on the one or more gears.

In another exemplary embodiment of the invention, interventional medical device includes an insertion tube assembly having an imaging tip at one end, and a control handle operably connected to the insertion tube opposite the transducer and adapted to be connected to an imaging system, wherein the control handle includes a body, a movement control mechanism disposed at least partially within the body, the movement control mechanism having one or more control elements disposed on the body, one or more gears rotatably disposed within the body and operably connected to the one or more control elements. The one or more gears including a number of engagement structures thereon and one or more cables engaged with the one or more gears, the one or more cables extending outwardly from the body and engaged with the imaging tip, and a motion locking mechanism disposed at least partially within the body, the motion locking mechanism having one or more brake rods biased into engagement with the engagement structures on the one or more gears and a release switch engaged with the one or more brake rods to selectively position the one or more brake rods into or out of engagement with the engagement structures on the one or more gears In still another exemplary embodiment of the method of the invention, a method for controlling the movement of an interventional medical device in an interventional medical procedure includes the steps of providing an interventional medical device having an insertion tube assembly having an imaging tip at one end and a control handle operably connected to the insertion tube opposite the transducer and adapted to be connected to an imaging system, wherein the control handle includes a body, a movement control mechanism disposed at least partially within the body, the movement control mechanism having one or more control elements disposed on the body, one or more gears rotatably disposed within the body and operably connected to the one or more control elements. The one or more gears including a number of engagement structures thereon and one or more cables engaged with the one or more gears, the one or more cables extending outwardly from the body and engaged with the imaging tip, and a motion locking mechanism disposed at least partially within the body, the motion locking mechanism having one or more brake rods biased into engagement with the engagement structures on the one or more gears and a release switch engaged with the one or more brake rods to selectively position the one or more brake rods into or out of engagement with the engagement structures on the one or more gears, operating the movement control mechanism to move the tip, and operating the motion locking mechanism to restrict movement of the movement control mechanism in one or more directions It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
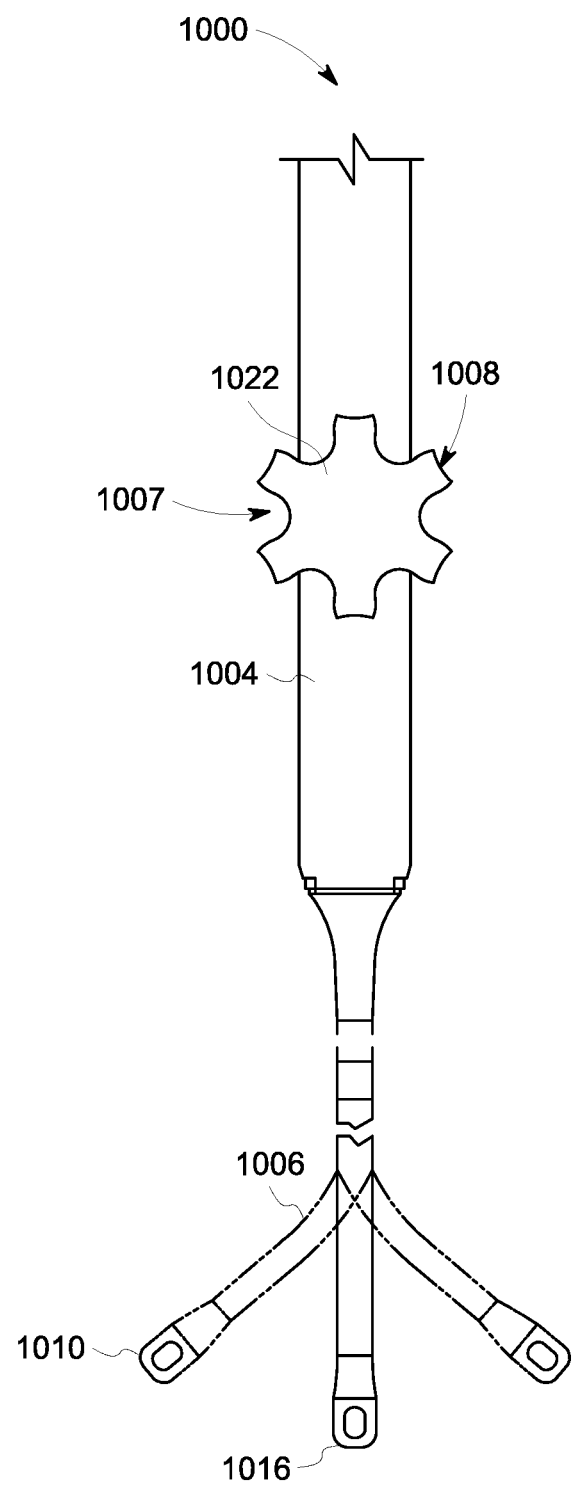
FIG. 1 is a top plan view of a prior art interventional probe including an insertion tube and a control handle.
Figure 2:
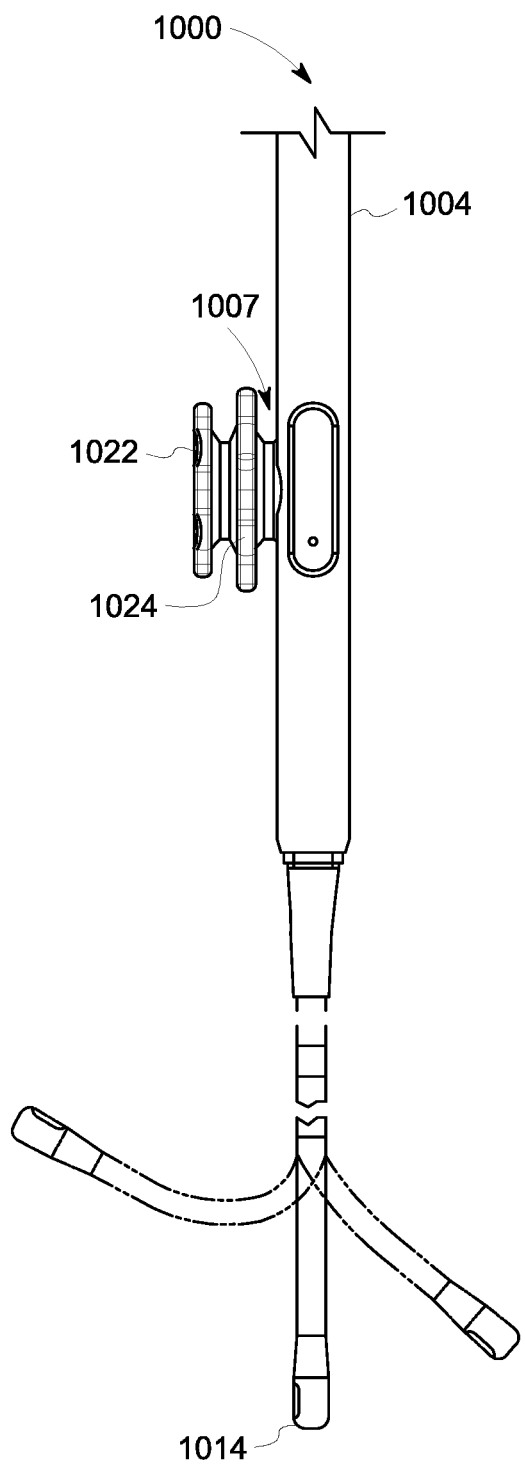
FIG. 2 is a side elevation view of the interventional probe of FIG. 1
Figure 3:
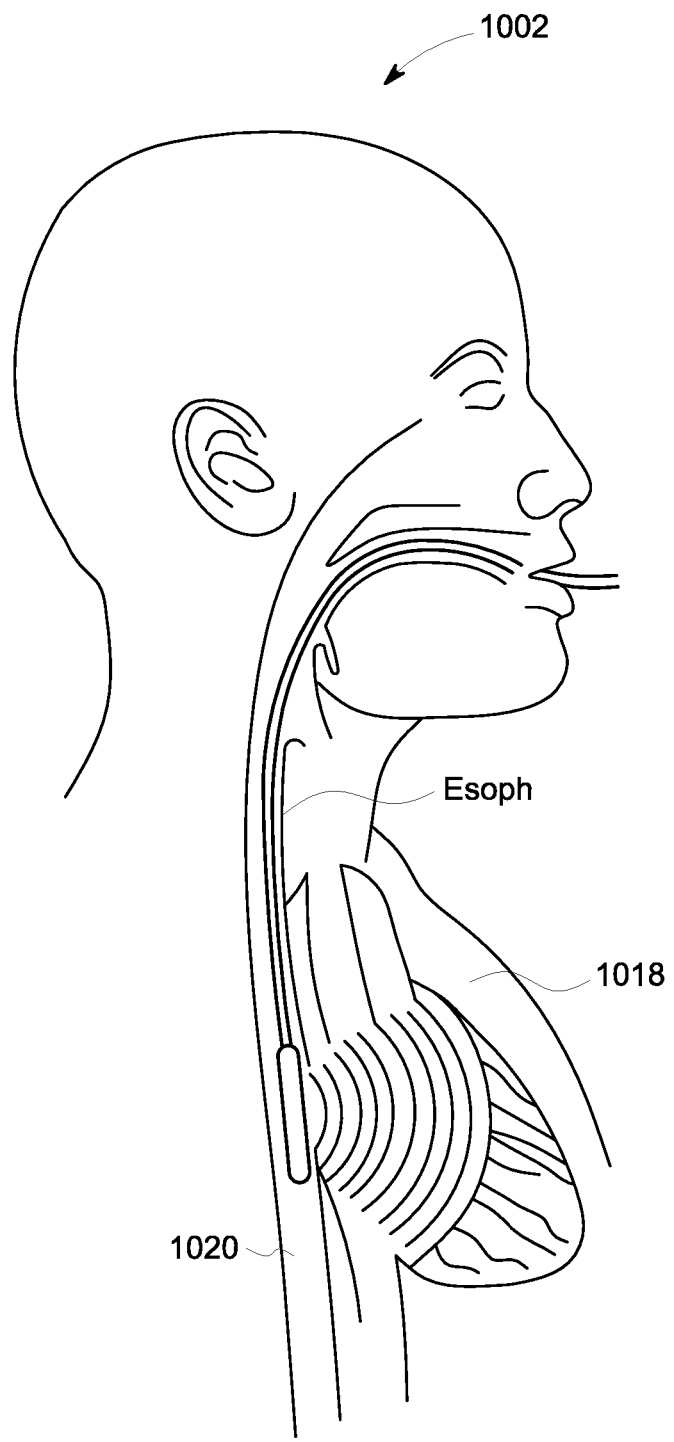
FIG. 3 is a schematic view of the interventional probe inserted within a patient.
Figure 4:
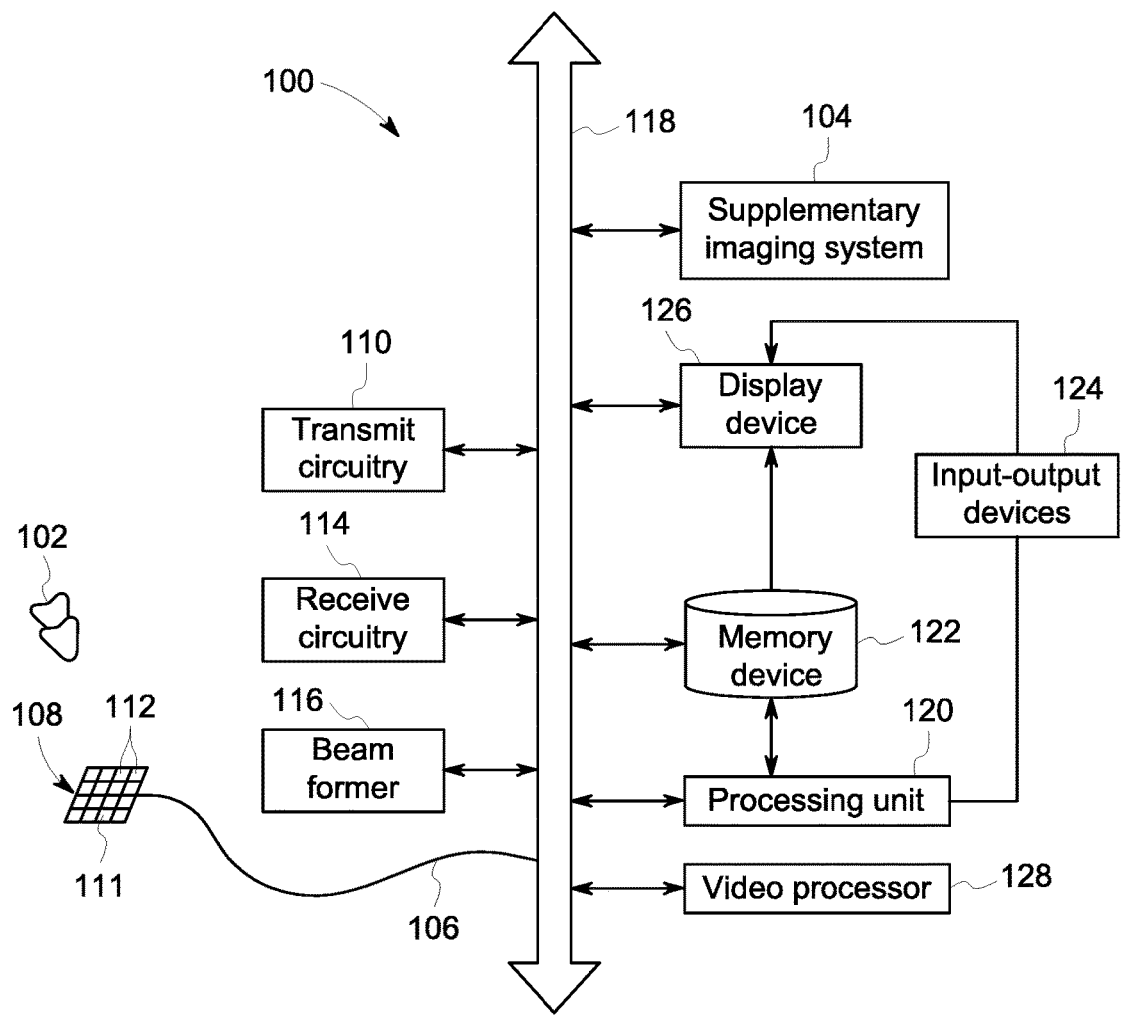
FIG. 4 is a schematic representation of an exemplary imaging system, in accordance with aspects of the present disclosure.

FIG. 4 illustrates an exemplary imaging system 100 for optimal visualization of a target structure 102 for use during interventional procedures. For discussion purposes, the system 100 is described with reference to a TEE system. However, in certain embodiments, the system 100 may be implemented in other interventional imaging systems such as a TTE system, a ICE system, an OCT system, a magnetic resonance imaging (MRI) system, a CT system, a positron emission tomography (PET) system, and/or an X-ray system. Additionally, it may be noted that although the present embodiment is described with reference to imaging a cardiac region corresponding to a patient, certain embodiments of the system 100 may be used with other biological tissues such as lymph vessels, cerebral vessels, and/or in non-biological materials.

In one embodiment, the system 100 employs ultrasound signals to acquire image data corresponding to the target structure 102 in a subject. Moreover, the system 100 may combine the acquired image data corresponding to the target structure 102, for example the cardiac region, with supplementary image data. The supplementary image data, for example, may include previously acquired images and/or real-time intra-operative image data generated by a supplementary imaging system 104 such as a CT, MRI, PET, ultrasound, fluoroscopy, electrophysiology, and/or X-ray system. Specifically, a combination of the acquired image data, and/or supplementary image data may allow for generation of a composite image that provides a greater volume of medical information for use in accurate guidance for an interventional procedure and/or for providing more accurate anatomical measurements.

Accordingly, in one embodiment, the system 100 includes an interventional device or probe 106 such as an ultrasound probe, a laparoscope, a bronchoscope, a colonoscope, a needle, a catheter and/or an endoscope. The interventional device 106 is adapted for use in a confined medical or surgical environment such as a body cavity, orifice, or chamber corresponding to a subject, e.g., a patient. The interventional device 106 may further include at least one imaging subsystem 108 disposed at a distal end of the interventional device 106. The imaging subsystem 108 may be configured to generate cross-sectional images of the target structure 102 for evaluating one or more corresponding characteristics. Particularly, in one embodiment, imaging subsystem 108 is configured to acquire a series of three-dimensional (3D) and/or four-dimensional (4D) ultrasound images corresponding to the subject, though the subsystem 108 can also obtain one-dimensional (1D) and two-dimensional (2D) ultrasound images. In certain embodiments, the system 100 may be configured to generate the 3D model relative to time, thereby generating a 4D model or image corresponding to the target structure such as the heart of the patient. The system 100 may use the 3D and/or 4D image data, for example, to visualize a 4D model of the target structure 102 for providing a medical practitioner with real-time guidance for navigating the probe/interventional device 106 within the patient.

To that end, in certain embodiments, the imaging subsystem 108 can be an ultrasound imaging system that includes transmit circuitry 110 that may be configured to generate a pulsed waveform to operate or drive an imaging element 111, such as one or more transducer elements 112. The transducer elements 112 are configured to transmit and/or receive ultrasound energy and may comprise any material that is adapted to convert a signal into acoustic energy and/or convert acoustic energy into a signal. For example, the transducer elements 112 may be a piezoelectric material, such as lead zirconate titanate (PZT), or a capacitive micromachined ultrasound transducer (CMUT) according to exemplary embodiments. The interventional device 106 may include more than one transducer element 112, such as two or more transducer elements 112 arranged in an array, or separated from each other on the interventional device 106. The transducer elements 112 produce echoes that return to the transducer elements 112 and are received by receive circuitry 114 for further processing. The receive circuitry 114 may be operatively coupled to a beamformer 116 that may be configured to process the received echoes and output corresponding radio frequency (RF) signals.

Further, the system 100 includes a processing unit 120 communicatively coupled to the acquisition/imaging subsystem 108, to operatively connect the processing unit 120 to the beamformer 116, the interventional device 106, and/or the receive circuitry 114, over a wired or wireless communications network 118. The processing unit 120 may be configured to receive and process the acquired image data, for example, the RF signals according to a plurality of selectable ultrasound imaging modes in near real-time and/or offline mode.

Moreover, in one embodiment, the processing unit 120 may be configured to store the acquired volumetric images, the imaging parameters, and/or viewing parameters in a memory device 122. The memory device 122, for example, may include storage devices such as a random access memory, a read only memory, a disc drive, solid-state memory device, and/or a flash memory. Additionally, the processing unit 120 may display the volumetric images and or information derived from the image to a user, such as a cardiologist, for further assessment on a operably connected display 126 for manipulation using one or more connected input-output devices 124 for communicating information and/or receiving commands and inputs from the user, or for processing by a video processor 128 that may be connected and configured to perform one or more functions of the processing unit 120. For example, the video processor 128 may be configured to digitize the received echoes and output a resulting digital video stream on the display device 126.

Figure 5:
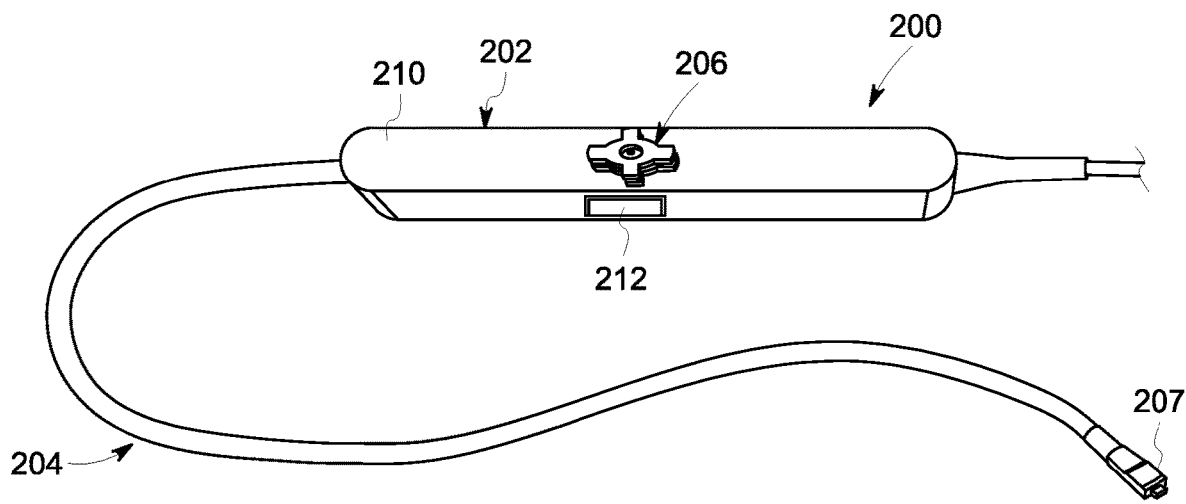
FIG. 5 is an isometric view of an interventional device including a control handle constructed according to an exemplary embodiment of the disclosure and operable with an ultrasound imaging system.
Figure 6:
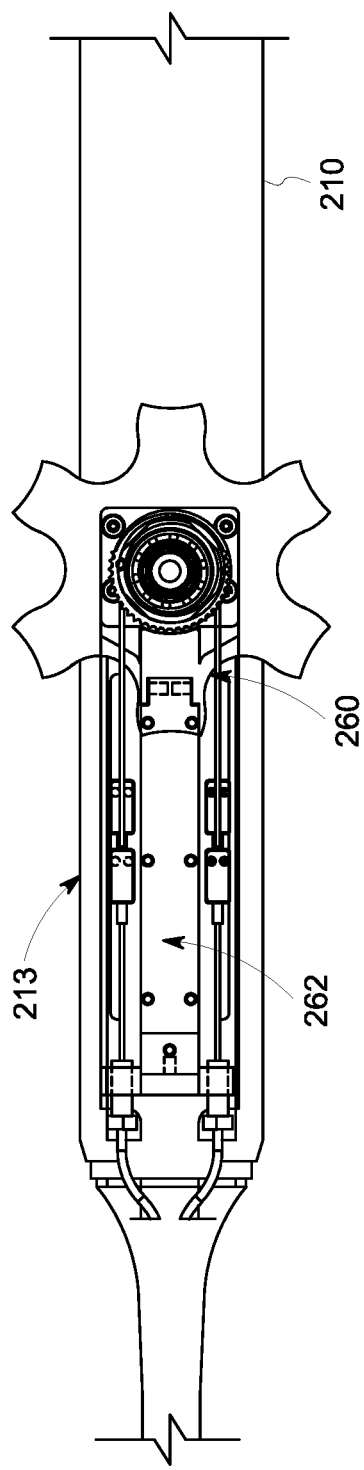
FIG. 6 is a partially broken away, top plan view of the control handle of FIG. 5 including a control mechanism according to an exemplary embodiment of the disclosure.
Figure 7:
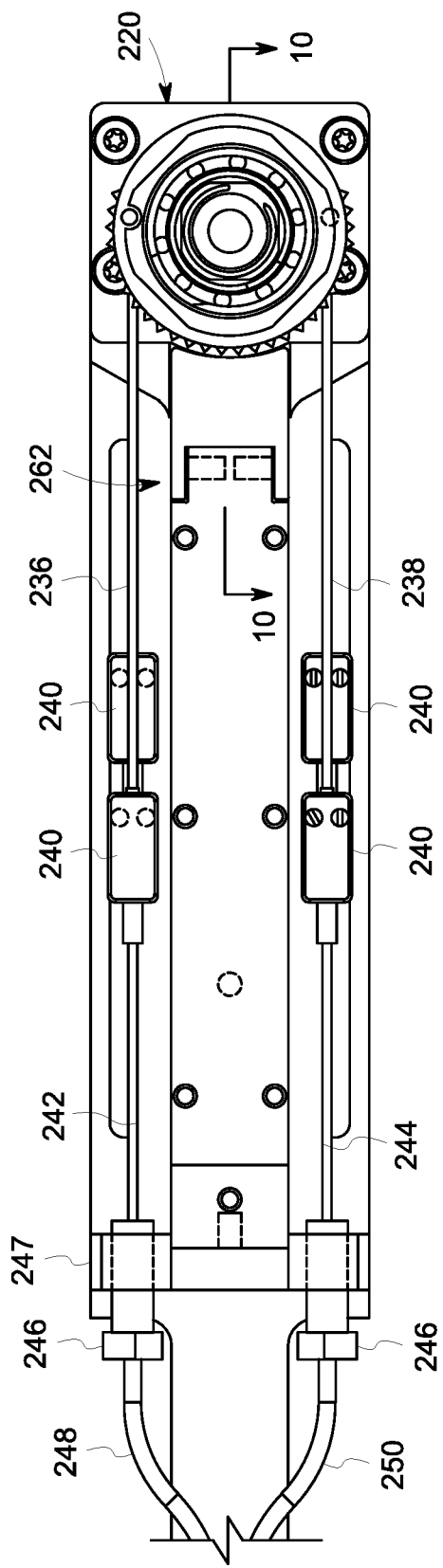
FIG. 7 is a partially broken away, top plan view of a control mechanism of the control handle of FIG. 6.
Figure 8:
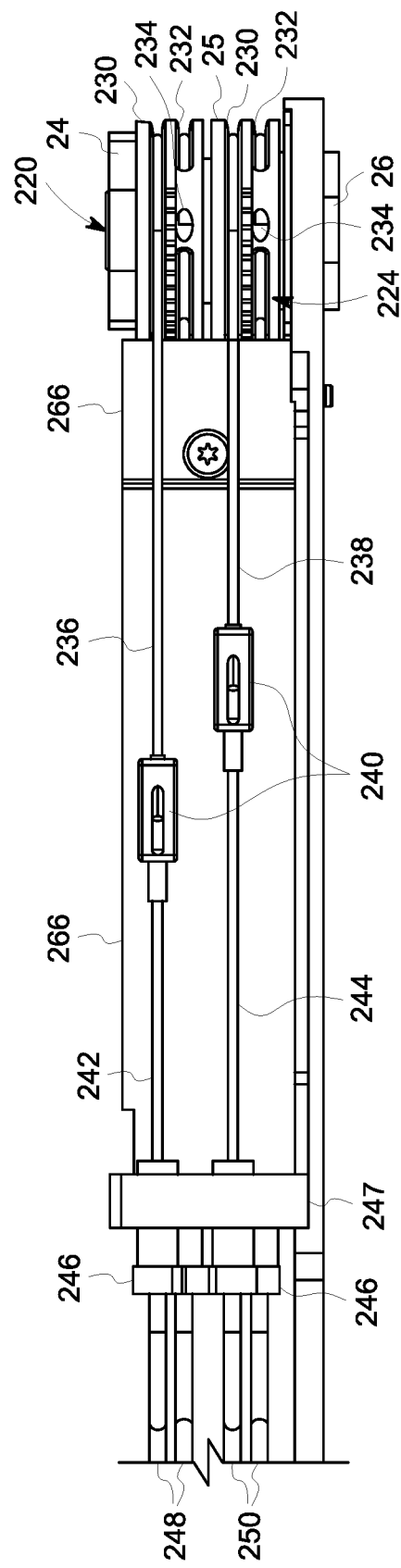
FIG. 8 is a partially broken away, side elevation view of the control mechanism of the control handle of FIG. 6.
Figure 9:
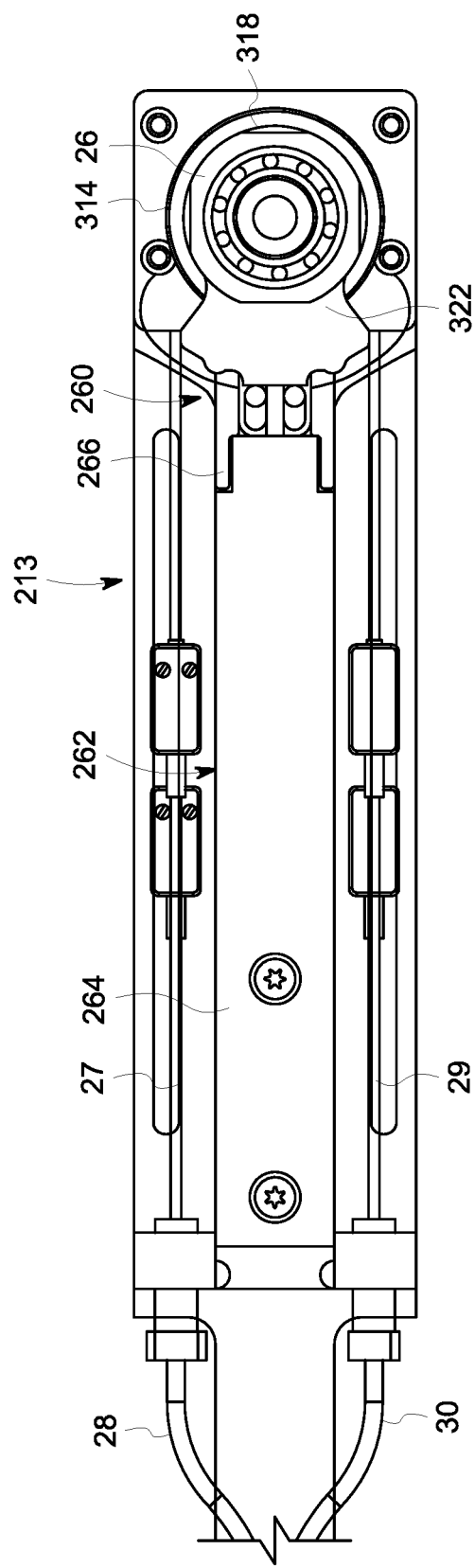
FIG. 9 is a partially broken away, bottom plan view of the control mechanism of the control handle of FIG. 6.

Referring now to FIG. 5, the interventional device 106 is disclosed in the illustrated exemplary embodiment as being formed as an ultrasound probe/TEE probe 200. The ultrasound probe 200 includes a control handle 202 that is operatively connected to the processing unit 120 via a cable 203, and an insertion tube 204 extending outwardly from the control handle 202 opposite the cable 203, where the tube 204 that includes a tip 207 opposite the handle 202 within which the imaging subsystem 108 is housed. The control handle 202 includes one or more control elements 206 thereon that enable the operator of the ultrasound probe 200 to control the various operations of the internal movement and imaging mechanisms, and associated wiring and/or other connections (not shown) disposed within hollow interior of the insertion tube 204.

Looking now at the illustrated exemplary embodiments of FIGS. 6-13, the control handle 202 includes an elongate body 210 formed of a lightweight and durable material to form the body 210, such as a plastic or a metal, and having any suitable construction to form the body 210, such as a one piece, a two piece, or other multiple piece construction.

The control elements 206 located on the body 210 can include one or more switches 212, buttons, or other elements 206, in conjunction with a movement control mechanism 213 formed with a pair of control wheels 214,216. The wheels 214, 216 are rotatably mounted to the exterior of the body 210 in configuration that enables the wheels 214, 216 to be readily engaged and rotated by an individual using the probe 200, such as the stacked configuration shown in the exemplary illustrated embodiment of FIGS. 6-10. The wheels 214,216 are each rotatably disposed around a fixed central shaft 218 that extends through and is secured to the body 210. The first wheel 214 is disposed adjacent the body 210 and is attached to a first gear 220 disposed within the body 210 around the central shaft 218. The second wheel 216 is located adjacent the first wheel 214 opposite the body 210 and includes a rotatable shaft 222 that extends through the first gear 220 and is attached to a second gear 224 disposed within the body 210 adjacent the first gear 220. A pair of bearings 226 are disposed between the second gear 224 and the central shaft 218 to enable the second gear 224 and second wheel 216 to rotate with respect to the central shaft 218 and the body 210. Another separate bearing 228 is disposed between the rotatable shaft 222 and the first gear 220 in order to enable the first gear 220 to rotate independently of the second gear 224 with respect to the central shaft 218 and the body 210.

The first gear 220 and the second gear 224 are formed similarly to one another and each includes a pair of spaced peripheral grooves 230,232 disposed thereon and defining a central ring 231 therebetween, where the central ring 231 includes a number of spaced teeth 233 spaced by grooves 235 (FIG. 7), or other suitable engagement structures disposed thereon. Each groove 230,232 includes a stop 234, with the stops 234 for each groove 230,232 located on opposed sides of the gear 220,224. A pair of control cables/wire ropes/stranded wires 236,238 are positioned within the respective grooves 230,232, with one end of each cable 236,236 engaged with the stop 234 in the groove 230,232. Opposite the stop 234, the control cables 236,238 are each engaged with separate connectors 240 that are also engaged opposite the control cables 236,238 with connector cables 242,244. The connector cables 242, 244 extend through an aligned bushing 246 located in a structural brace 247 disposed within the body 210 and spaced from the gears 220,224. The bushings 246 maintain the vertical and horizontal orientation of the control cables 236,238 and connector cables 242,244 in alignment with the grooves 230,232, thereby preventing the cables 236,238,242,244 from interfering with one another when moved by the rotation of the gears 220,224. Alternatively, the control cables 236,238 and the connector cables 242,244 can be formed as unitary cables, eliminating the need for the connectors 240.

From the bushings 246, the connector cables 242,244 extend through cable guides 248,250 connected to the bushing 246 and located along the insertion tube 204. The connector cables 242,244 and guides 248,250 terminate and are connected to opposite sides (top and bottom or left and right) of the tip 207, such that a cable loop is formed between each of the gears 220,224 and the tip 207, enabling rotation of the gears 220,224 to translate into linear motion, i.e., anterior/posterior or right/left, of the tip 207 while utilizing the movement control mechanism 213.

Figure 10:
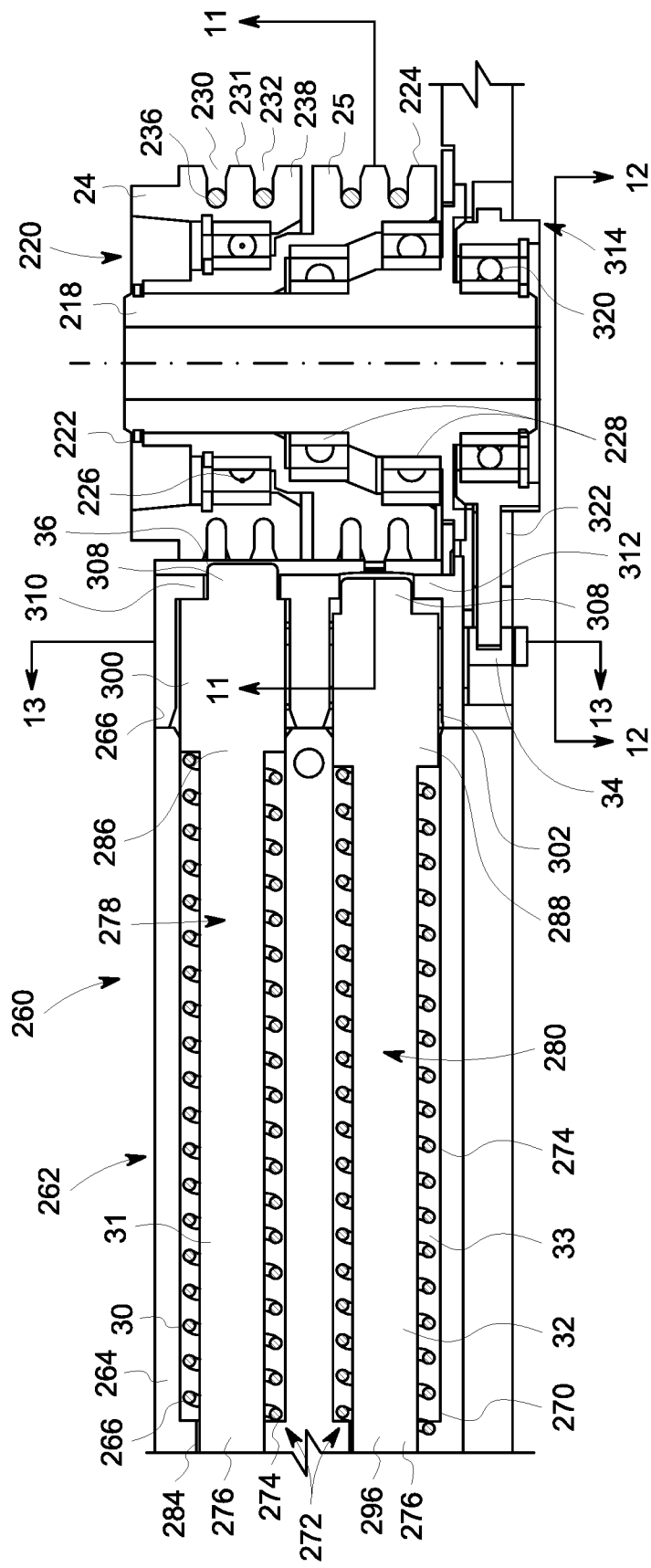
FIG. 10 is a cross-sectional view along line 10-10 of FIG. 7 illustrating a deflection lock mechanism according to an exemplary embodiment of the present disclosure.

Looking now at FIGS. 6-14, the probe 200 additionally includes a motion locking mechanism 260 that is engaged with the gears 220, 240. The locking mechanism 260 includes a housing 262 disposed within the body 210 between the control cables 236,238. The housing 262 includes a first portion 264 located adjacent the brace 247 and a second portion 266 located adjacent the gears 220,224. As best shown in FIG. 10, the first portion 264 includes a pair of blind bores 268,270 formed in the first portion 264 in alignment with the first gear 220 and second gear 224, respectively. The bores 268,270 each receive a biasing member 272 therein, which in the illustrated exemplary embodiment is a compression spring 274, such as, a wave spring or a coil spring, among other suitable types of biasing members. The compression spring 274 receives the stem 276 of a brake rod 278,280 therein. The stem 276 extends through the central space 282 defined within the compression spring 274 into an alignment channel 284 disposed at the end of each of the bores 268,270 to maintain the alignment of the stem 276 with regard to the bore 268,270.

Opposite the stem 276, the brake rods 278,280 each include a head 286,288 on which is disposed a wedge 308 opposite the stem 276. Each head 286,288 that has at least one dimension larger than the space 282 defined within the center of the compression spring 274, such that each head 286,288 seats on and engages the end of the compression spring 274 opposite the channel 284. Additionally, the heads 286,288 of each brake rod 278,280 are shaped to be slightly less in size than the bores 268,270 so that the heads 286,288 remain aligned with the bores 268,270 as they move along the bores 268,270.

As best shown in FIGS. 10-13, each of the heads 286,288 includes an arm 292,294 that extends outwardly from the respective head 286,288, which in the illustrated exemplary embodiment is shown as a direction generally perpendicular to the long axis 296 of each brake rod 287,280. In addition, the head 288 on brake rod 280 is formed with a recess 298 disposed below head 286 on brake rod 278 and through which the arm 292 extends. The recess 298 has dimensions to enable the arm 292 to extend through the recess 298 without contacting the perimeter of the recess 298. Further, each arm 292,294 extends through an aligned aperture 300,302 in the second portion 266 to terminates opposite the respective head 286,288 in an aligned position outside of the second portion 266.

At the end of each of the arms 292,294 outside of the second portion 266, the arms 292,294 each include a pin 304 engaged with and extending outwardly from the arms 292, 294. The pins 304 in the illustrated exemplary embodiment are generally cylindrical in shape and include a tab 305 located opposite the arms 292,294. Each pin 304 includes a bearing sleeve 306 disposed around the pin 304 between the arm 292,294 and the tab 305 that is rotatable with respect to the pin 304 and retained on the pin 304 by the tab 305.

Figure 11:
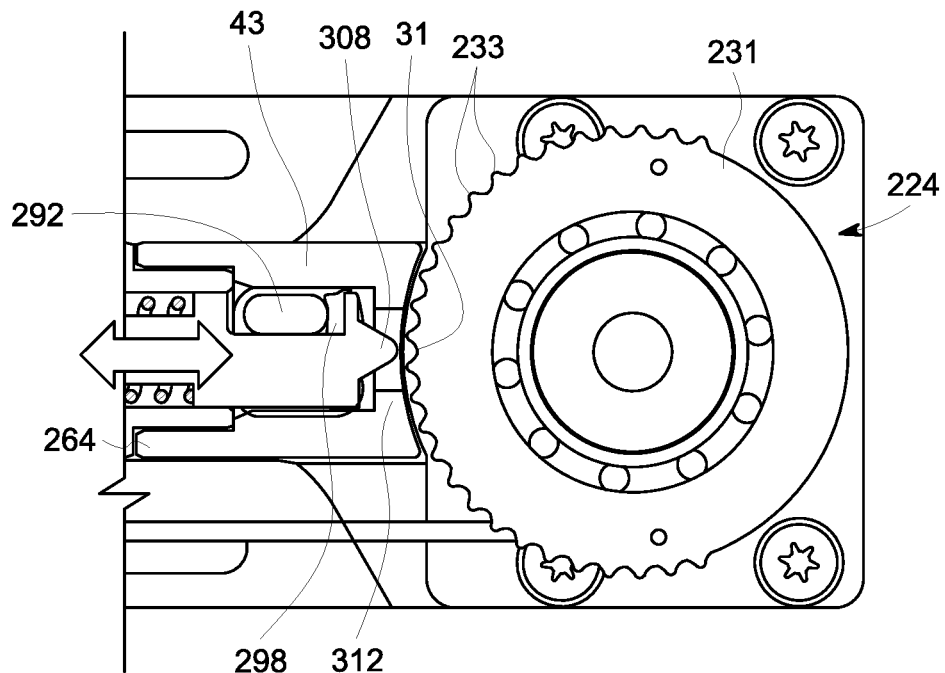
FIG. 11 is a cross-sectional view along line 11-11 of FIG. 10.
Figure 12:
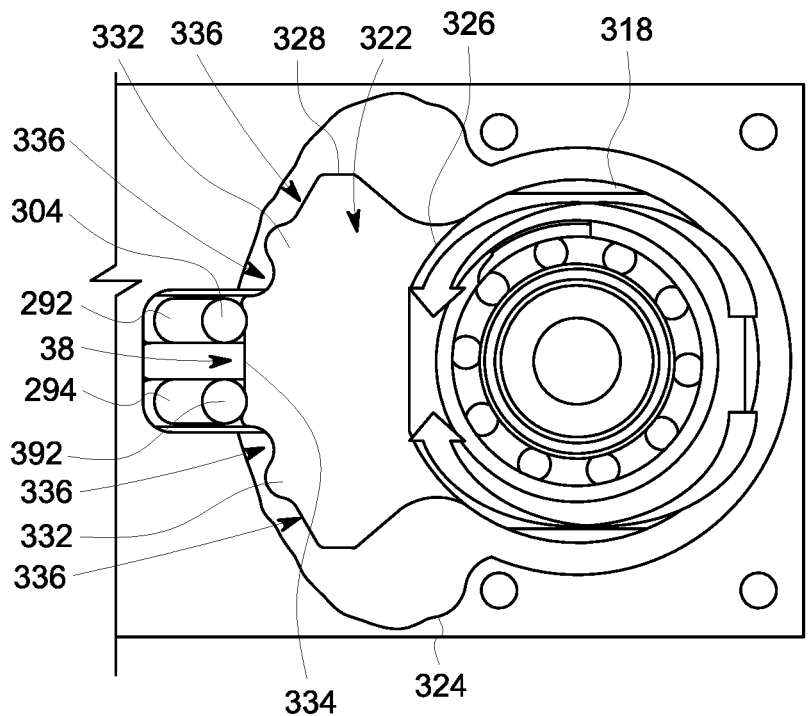
FIG. 12 is a cross-sectional view along line 12-12 of FIG. 10.
Figure 13:
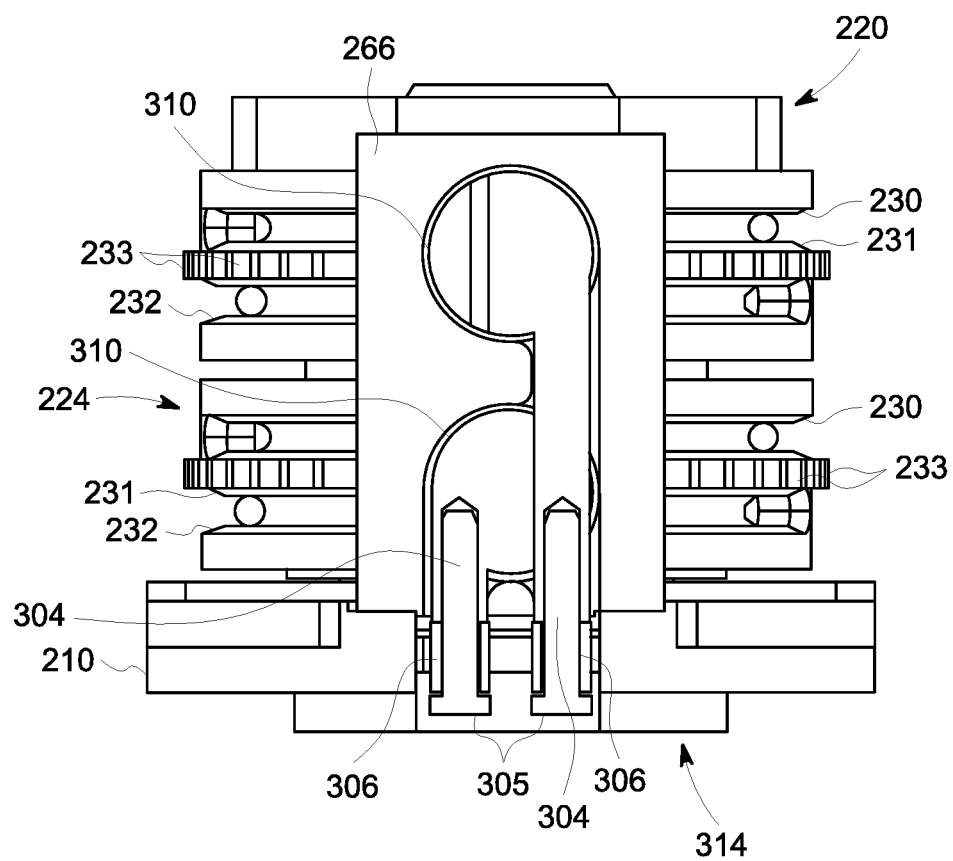
FIG. 13 is a cross-sectional view along line 13-13 of FIG. 10.

Looking now at FIGS. 10 and 11, opposite the stems 276 each head 286,288 includes the wedge 308 formed thereon. Each wedge 308 projects outwardly from the respective head 286,288 in a direction along the long axis 296 of the brake rods 278,280 and is aligned with an opening 310,312 in the second portion 264 generally opposite the first portion 264. Due to the engagement with the springs 274, the heads 286,288 are continuously biased to urge the wedges 308 into and through the associated aligned openings 310,312, as illustrated by the position of brake rod 278 in FIG. 10. In this position, the wedge 308 is inserted within a groove 235 on the central ring 231 of the gear 220 between adjacent teeth 233 that are engaged by the wedge 308, thereby preventing the rotation of the gear 220 and the associated wheel 214.

Referring now to FIGS. 9-12, in order to disengage or move the wedge 308 out of the groove 235 and engagement with the teeth 233, the motion locking mechanism 260 includes a release switch 314. In the illustrated exemplary embodiment, the release switch 314 is formed with a actuator/knob 316 disposed on the body 210 over the central shaft 218 opposite the wheels 214,216. The knob 316 is connected to a cam 318 that is located at least partially within the body 210 around the central shaft 218 in a position adjacent the second gear 224 opposite the first gear 220. A bearing 320 is disposed between the cam 318 and the central shaft 218 to enable the cam 318 to rotate with respect to the central shaft 218 independently of both the first gear 220 and the second gear 224.

The cam 318 includes an engagement flange 322 that extends outwardly from the cam 318 into a recess 324 formed in the body 310 adjacent the cam 318. The shape of the flange 322 and the recess 324 are complementary to one another to allow the flange 322 to rotate freely within the recess 324 as a result of the movement of the third gear 318 around the central shaft 218. In the illustrated exemplary embodiment, the flange 322 is formed with a fan-shape, having a curved narrow end 326 attached to the cam 318 and a curved wide end 328 opposite the narrow end 326. The wide end 328 is formed with a number of notches 330 therein separated by ridges 332, including a wide shallow central notch 334, and a number of smaller deep side notches 336 disposed on each side of the central notch 334. The position and length of the flange 322 between the narrow end 326 and the wide end 328 enables the pins 304 on each arm 292,294 to be engaged within one of the notches 330 on the flange 322. The engagement of the flange 322 with the pins 304 opposes the bias of the spring 274, such that the flange 322 can selectively press the pins 304 and the brake rods 278,280 into the second portion 266 of the housing 262 to move the wedges 308 out of the grooves 235 between the teeth 233 on one or both of the gears 220,224, thereby disengaging the wedges 308 from the teeth 233.

Looking now at FIGS. 10, 12 and 14A-14D, the depth of the shallow central notch 334 is less than the depth of the deep side notches 336, which enable the central notch 334 to press the pins 304 and brake rods 278,280 into the housing 262 against the bias of the spring 274. The greater depth of the side notches 336 enable the spring 274 to press the pins 304 into the notches 336 to a position where the wedge 308 on the brake rod 278,280 associated with the pin 304 disposed within the notch 336 is able to engage the teeth 233 on the aligned gear 220,224.

Figure 14A:
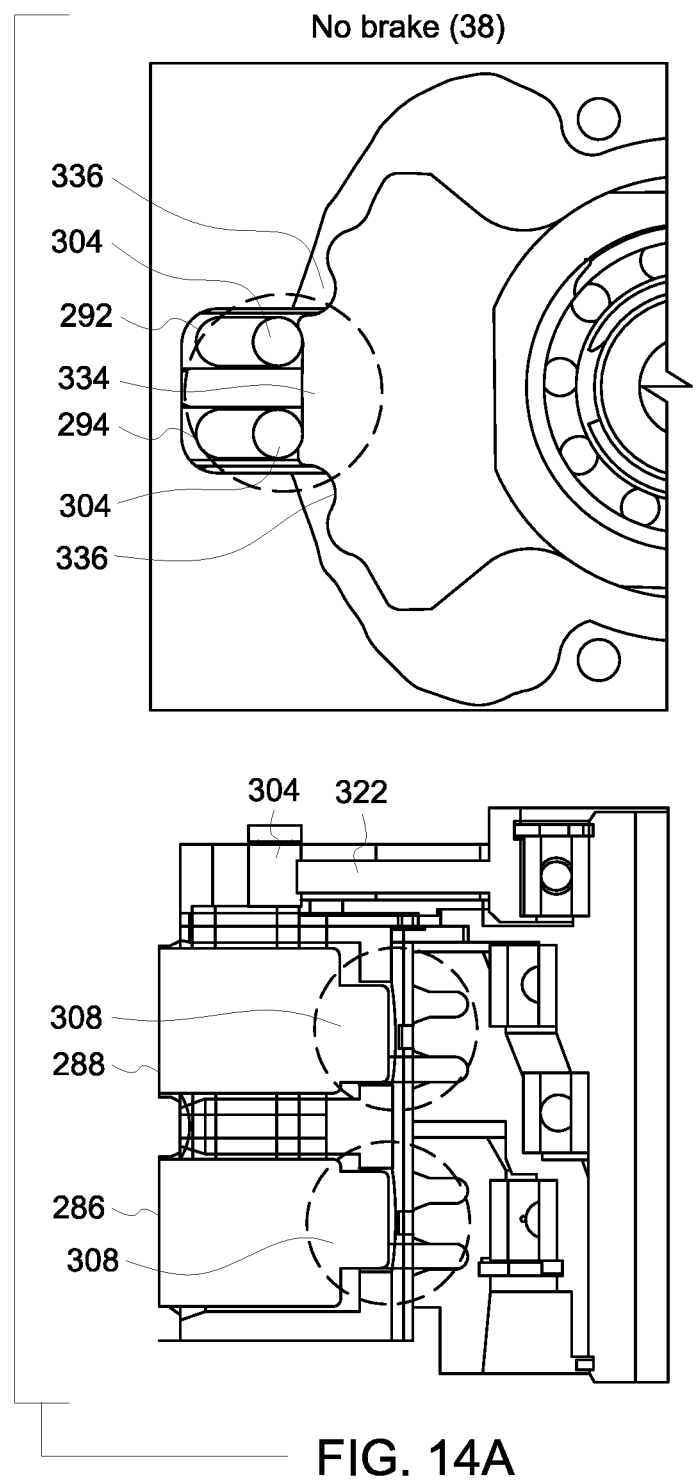
FIGS. 14A-14D are partially broken away cross-sectional and bottom plan views of the various operating configurations of the deflection lock mechanism of FIG. 9.

In FIGS. 14A-14D, the different operational positions of the release switch 314 are illustrated. In FIG. 14A, both of the pins 304 are located within the central notch 334. In this position, the flange 332 engages and presses the pins 304, and by extension both locking rods 278,280 into the housing 262 against the bias of the spring 274. Thus, the wedges 308 on each locking rod 278,280 are spaced from the teeth 233 on the gears 220,224, enabling each gear 220,224 to be freely rotated to operate the movement control mechanism 213 to position the tip 207 where desired in each of the AP and RL planes.

Figure 14B:
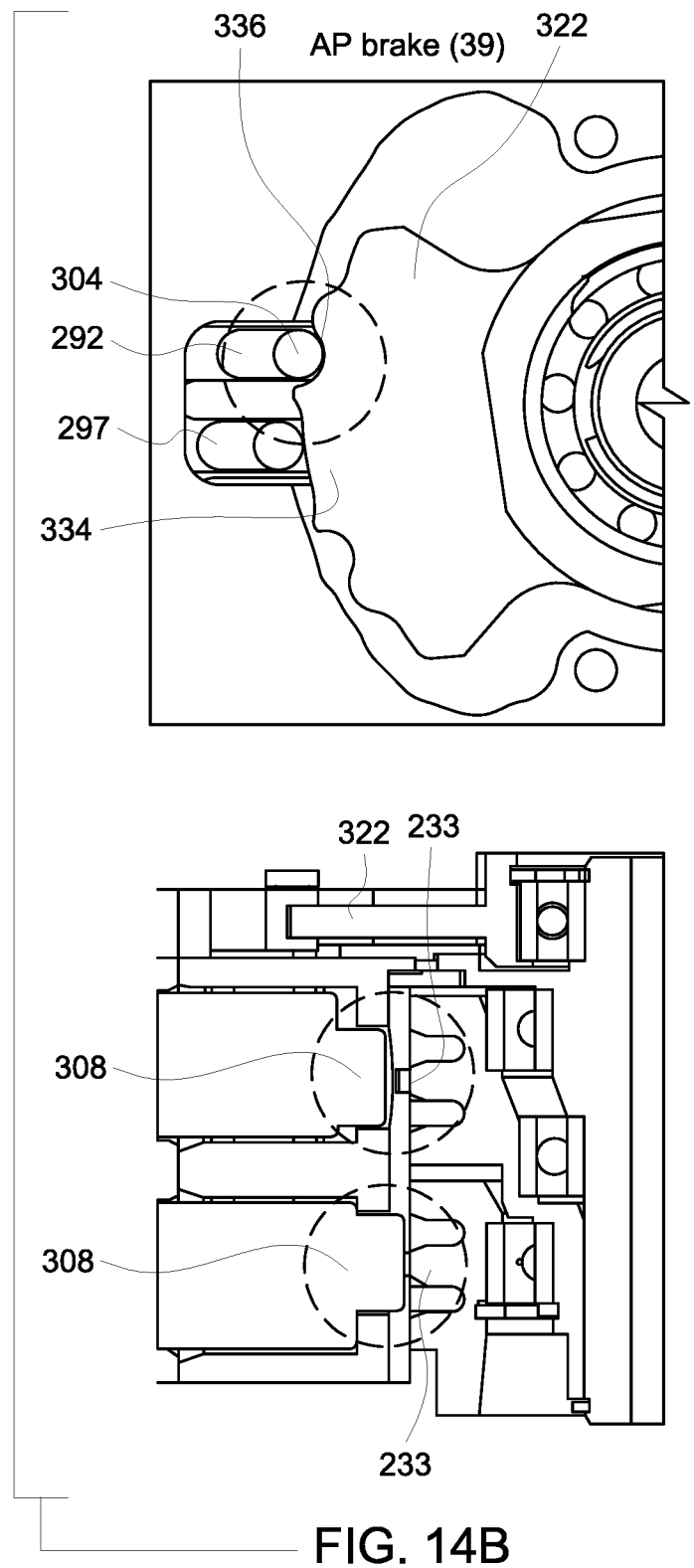

Looking now at FIG. 14B, when the release switch 314/cam 318 is rotated counterclockwise with reference to the exemplary orientation shown in FIG. 14B, the pin 304 associated with the locking rod 278 is pressed further into the housing 262 by the ridge 332, until the pin 304 is aligned with the notch 336. Due to the depth of the notch 336, when the pin 304 for the braking rod 278 is seated in the notch 336, the braking rod 278 is moved out of the housing 262 into a position where the wedge 308 on the rod 278 contacts and engages the teeth 233 on the first gear 220. Due to this engagement of the wedge 308 on rod 278 with the teeth 233 on the gear 220, the free rotation of the gear 220 is stopped, consequently locking the gear 220 in that position. The tip 207 is consequently locked or retained in the AP or RL position or orientation designated by the particular position of the first gear 220. However, the pin 304 associated with the braking rod 280 is retained within the central notch 334, such that the braking rid 280 remains disengaged from the second gear 224, allowing free movement of the second gear 224, and thus the tip 207 in the associated AP or RL plane.

Figure 14C:
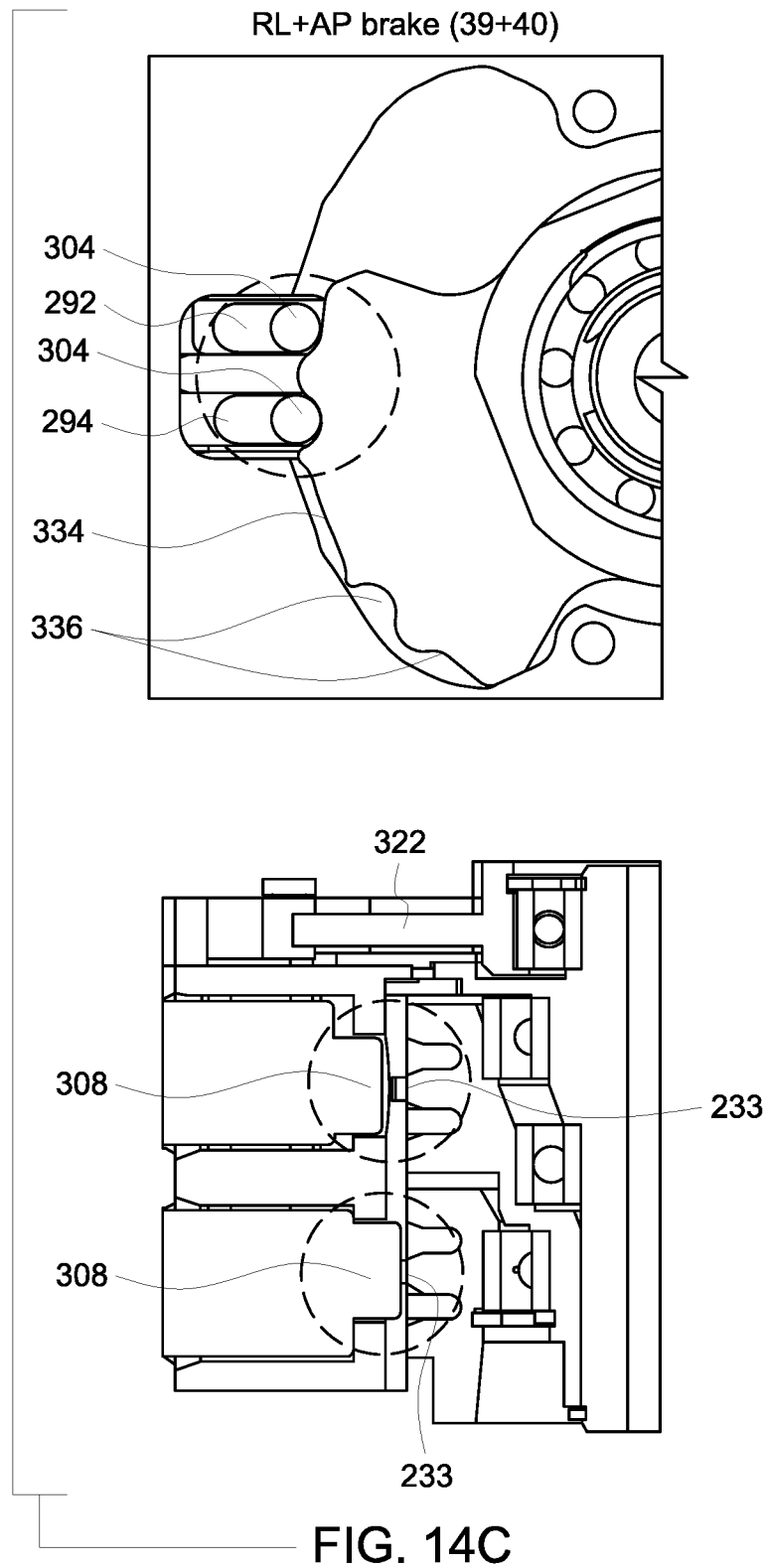

With regard to FIG. 14C, the release switch 314/cam 318 is rotated further in a clockwise orientation from the position in FIG. 14B, such that each of the pins 304 are seated within notches 336. Due to the depth of the notches 336, both rods 278,280 are allowed to move their wedges 308 into engagement with the aligned first gear 220 and second gear 224, such that rotation of each of the gear 220,224 is stopped, preventing any movement of the tip 207 using the wheels 214,216.

Figure 14D:
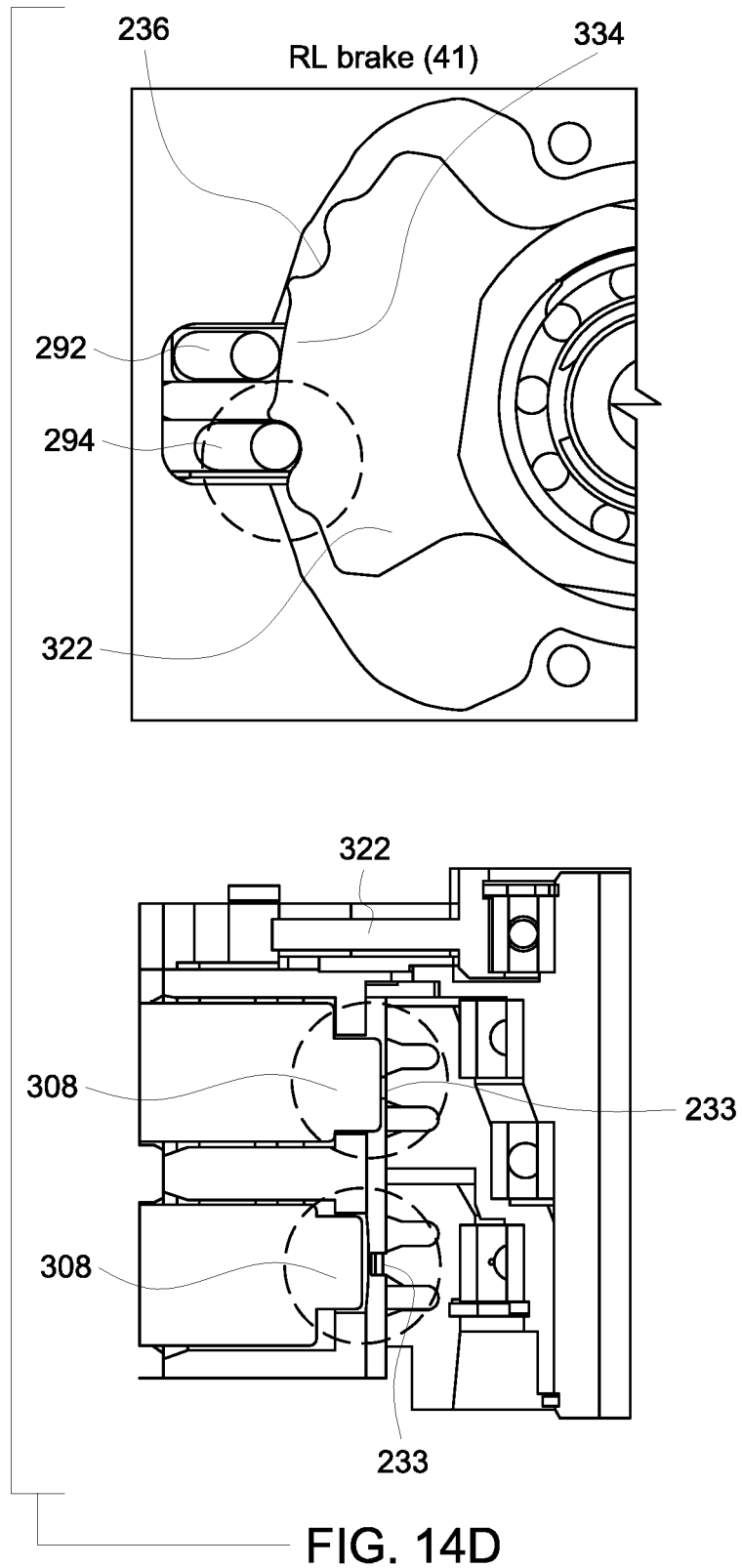

Similarly to the configuration of FIG. 14B, looking now at FIG. 14D, when the release switch 314/cam 318 is rotated in a clockwise direction relative to the exemplary orientation of FIG. 14D, the pin 304 associated with the braking rod 280 is moved out of the central notch 334 and into an adjacent notch 336, while the pin 304 for rod 278 remains within the central notch 334. In this position, the wedge 308 on rod 280 engages the teeth 233 on the second gear 224, while the wedge 308 on the rod 278 remains disengaged from the first gear 220. As such, the tip 207 is stopped from being moved in the associated AP or RI, plane by movement of the second gear 224, while movement of the tip 207 in the other of the AP or RL planes by rotation of the first gear 220 is allowed. Further, though not shown in FIGS. 14A-14D, further rotation of the release switch 314/cam 318 in the clockwise direction of FIG. 14D places each of the pins 304 in notches 336 to one side of the central notch 334 opposite the configuration of FIG. 14C, but that enables the rods 278,280 to both engage the gears 220,224 to prevent movement of the tip 207 in both the AP and RL planes, identically to the configuration shown in FIG. 14C.

Figure 15A:
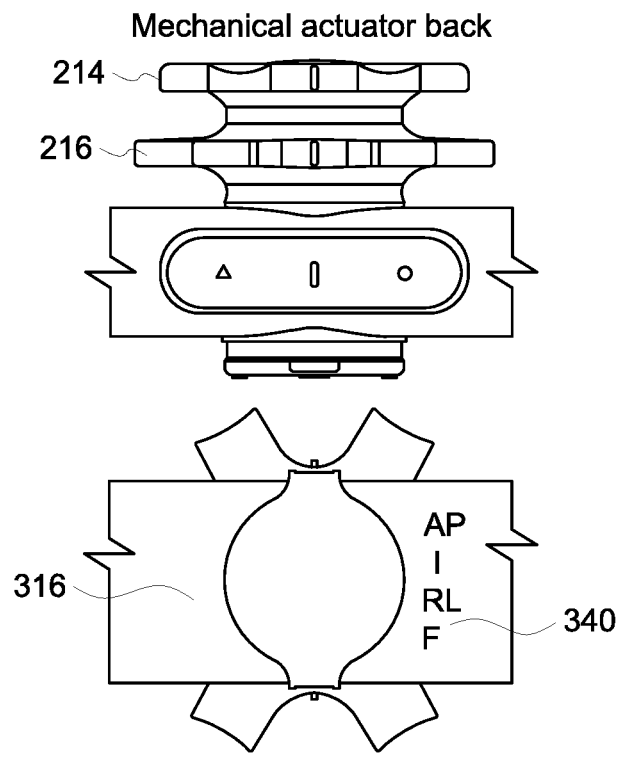
FIGS. 15A-15E are top and bottom plan views of different locations on the control handle for a control switch for operation of the deflection lock mechanism according to exemplary embodiments of the disclosure.
Figure 15B:
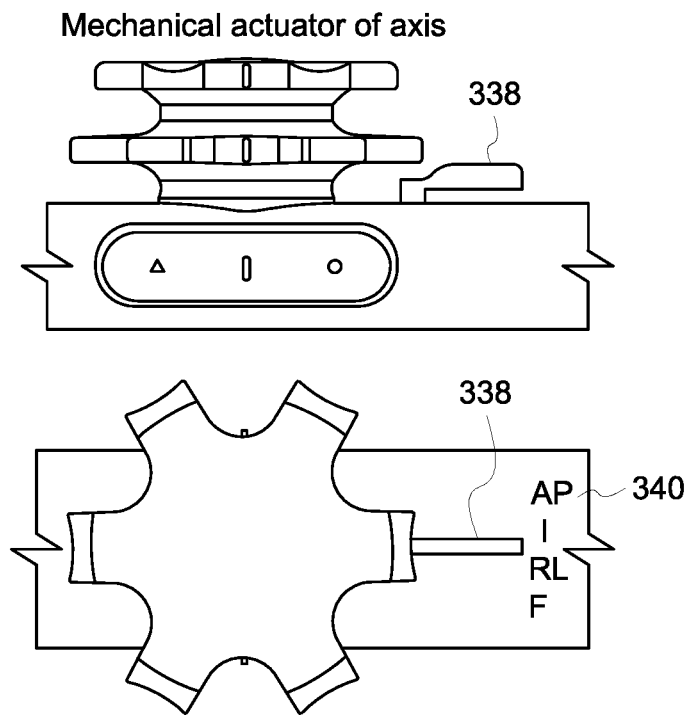
Figure 15C:
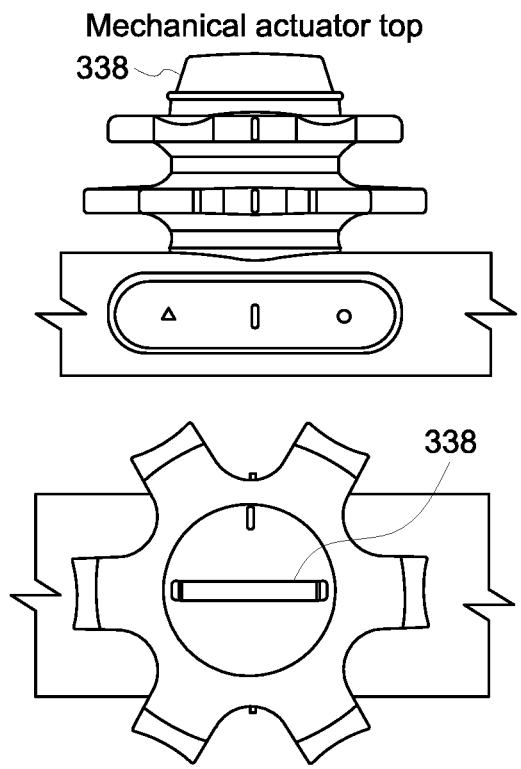
Figure 15D:
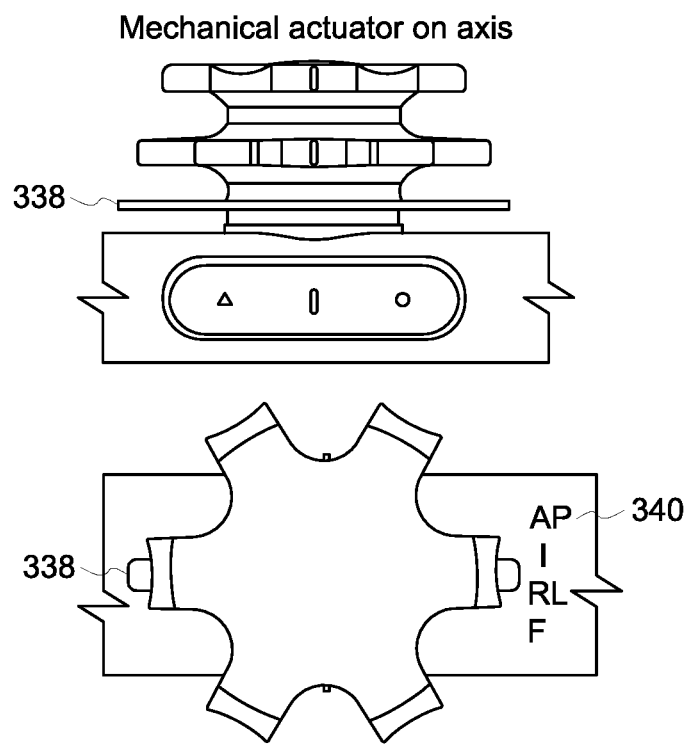
Figure 15E:
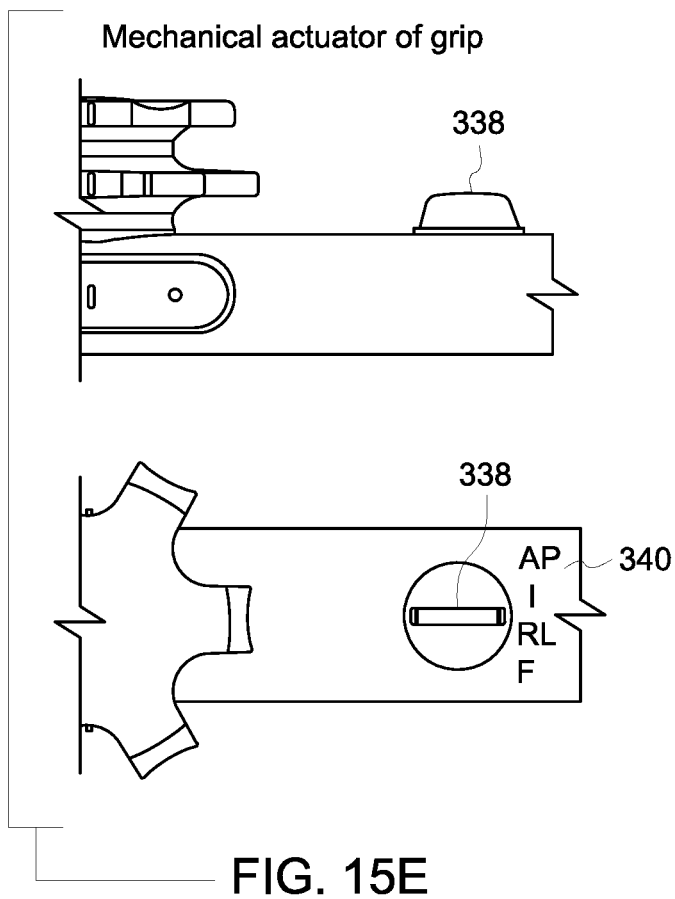

Looking now at FIGS. 15A-15E, in place of the knob 316, the release switch 314/cam 318 includes an actuator 338 connected to the cam 318 and disposed on and/or over the exterior of the body 310. The actuator 338 enables the user to rotate the cam 318 and the flange 322 within the body 210 in order to select the desired operational configuration for the motion locking mechanism 260. Indicia 340 can be placed on or adjacent the actuator 338 on order to illustrate the positions of the actuator 338 that are associated with the various operating configurations of the motion looking mechanism 260. Further, as shown in each of FIGS. 15A-15E, the actuator 338 can take various forms and be located in different positions on the exterior of the body 210, e.g., in alignment with the wheels 214,216 (FIGS. 15A, 15C and 15D) or adjacent the wheels 214,216 (FIGS. 15B and 15E).

As described previously, each of the rods 278,280 are engaged with springs 274 in the housing 262 that have biasing forces acting on the rods 278,280 that can be overcome by the rotation of the release witch 314 to enable the motion locking mechanism 260 to selectively allow movement of the tip 207 utilizing the movement control mechanism 213. The biasing force provided by the spring(s) 274 is also able to be overcome when a sufficient rotational force/torque is applied to one or both of the wheels 214,216 to rotate the gear(s) 220,224 when the wedge(s) 308 are engaged with the gear(s) 220,224, such as when the user overrides the motion locking mechanism 260 in emergency situations and/or when a force exerted on the tip 207 inside the patient 202 is too high, and could result in damage to the tip 207 and/or injury to the patient 202. In one exemplary embodiment, the spring 274 is selected to provide a biasing force on the rods 278,280 that is high enough to prevent any inadvertent rotation of the wheels 214,216 from overriding the motion locking mechanism 260, but that is below the force threshold for causing damage to the tissue of the patient 202. However, the structure of the teeth 233 and the wedges 308, e.g., with each including sloped engagement surfaces, allows the teeth 233 and wedges 308 to slide with regard to one another when forces exceeding the biasing force of the spring 274 are exerted on the tip 207 and/or the wheel(s) 214,216, while enabling the teeth 233 and wedges 308 to readily re-engage one another in a ratchet-like fashion, thus maintaining the engagement of the motion locking mechanism 260 after accommodation for the applied excessive force.

Figure 16:
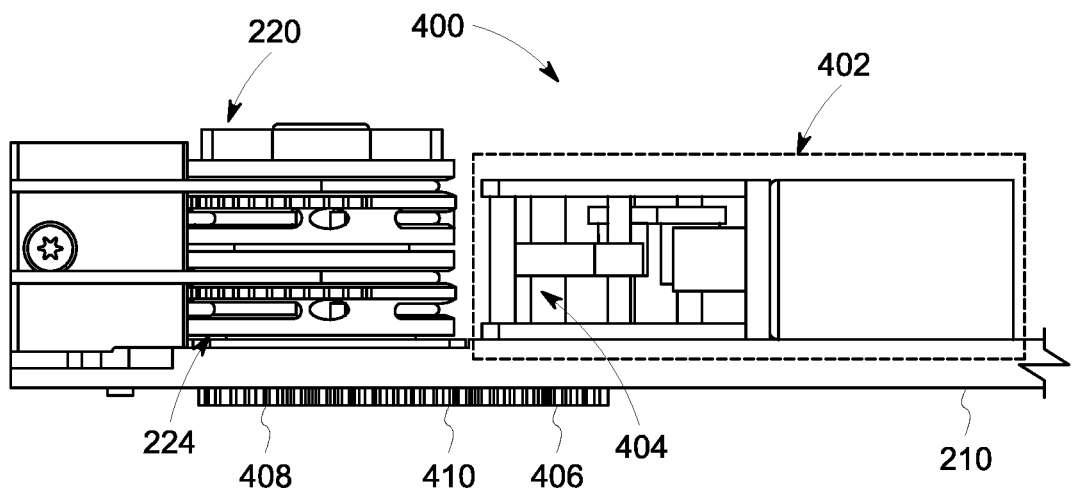
FIG. 16 is a partially broken away, cross-sectional view of an electronic deflection lock mechanism according to an exemplary embodiment of the disclosure.
Figure 17:
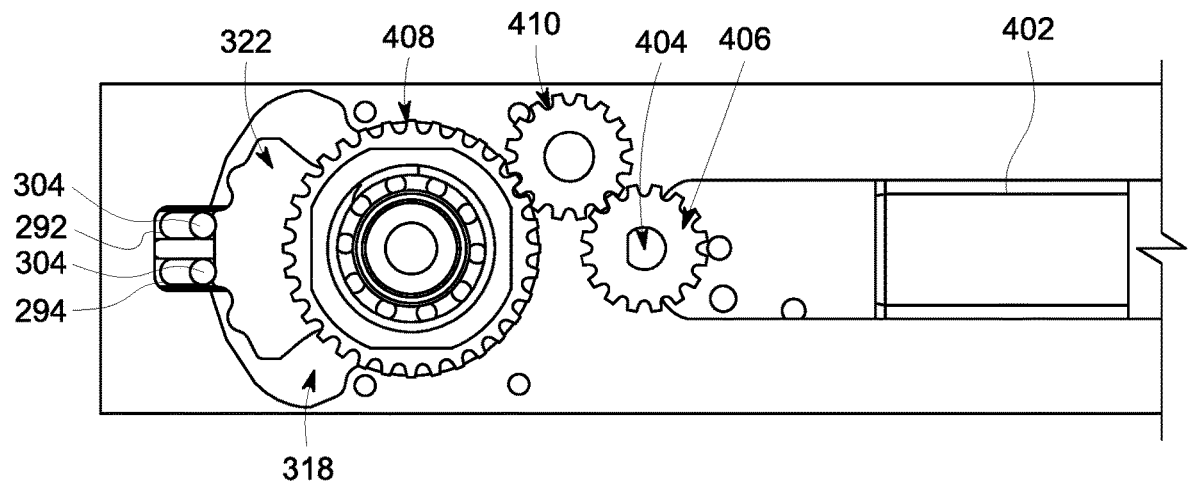
FIG. 17 is a bottom plan view of the electronic deflection lock mechanism of FIG. 16.
Figure 18:
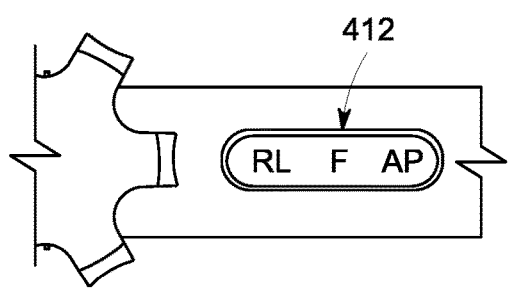
FIG. 18 is a top plan view of a control switch for operation of the electronic deflection lock mechanism.

Looking at the illustrated exemplary embodiment of FIGS. 16-18, a motion locking mechanism 400 for a probe 200 is shown that includes a motor 402 located within the body 210. The motor 402 is an electric motor, such as high torque, direct current (DC) motor, that can be powered via the cable 203, or using a rechargeable power source (not shown), such as a rechargeable battery or an induction-charged power source, and has a drive shaft 404 that engages a first spur gear 406 to rotate the spur gear 406. The first spur gear 406 can be directly engaged with a driven gear 408 operably connected to the cam 318, or to a second spur gear 410 disposed between the first spur gear 3406 and the driven gear 408. When rotated by the motor 402, the driven gear 408 rotates the cam 318 and the flange 322 to position the flange 322 and notches 334,336 thereon in the desired configuration for the motion locking mechanism 400, as described with respect to FIGS. 14A-14D. Further, the actuator 412 for the mechanism 400 is formed of a suitable electric switch 414, such as a membrane switch, including indicia 416 thereon showing the locations for the portion of the switch 414 associated with a particular configuration for the mechanism 400.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A control handle for an interventional medical device, the control handle comprising:
    a body;
    a movement control mechanism disposed at least partially within the body, the movement control mechanism comprising:
        a pair of axially aligned control elements disposed on the body;
        a pair of axially aligned gears rotatably disposed within the body and operably connected to the pair of axially aligned control elements, the pair of axially aligned gears including engagement structures thereon; and
        one or more cables engaged with the pair of axially aligned gears, the one or more cables extending outwardly from the body and adapted to be engaged with a tip of the interventional medical device; and
    a motion locking mechanism disposed at least partially within the body, the motion locking mechanism comprising:
        one or more brake rods biased into engagement with the engagement structures on the pair of axially aligned gears; and
        a release switch engaged with the one or more brake rods to selectively position the one or more brake rods into or out of engagement with the engagement structures on each of the pair of axially aligned gears.

2. The control handle of claim 1, wherein the motion locking mechanism includes one or more springs biasing the one or more brake rods.

3. The control handle of claim 2, wherein the one or more springs are compression springs.

4. The control handle of claim 3, wherein the one or more brake rods comprise:
    a stem disposed within the one or more compression springs; and
    a head disposed against an end of the compression spring.

5. The control handle of claim 1, wherein the one or more brake rods include a pin extending outwardly from the one or more brake rods and engaged with the release switch.

6. The control handle of claim 5, wherein the release switch includes an engagement flange having multiple notches that receive the pin therein.

7. The control handle of claim 6, wherein the release switch includes an actuator disposed on the exterior of the body.

8. The control handle of claim 7, wherein the release switch further comprises a motor operably connected between the actuator and the engagement flange.

9. The control handle of claim 6, wherein the multiple notches include one or more shallow notches and one or more deep notches.

10. The control handle of claim 1, wherein the one or more brake rods include a wedge that is selectively engaged with the engagement structures on the pair of axially aligned gears.

11. The control handle of claim 10, wherein the engagement structures are formed as teeth on the pair of axially aligned gears.

12. The control handle of claim 1, wherein the pair of axially aligned control elements include a pair of axially aligned control wheels each engaged with one of the pair of axially aligned gears.

13. An interventional medical device comprising:
    an insertion tube assembly having an imaging tip at one end; and
    a control handle operably connected to the insertion tube opposite the imaging tip and adapted to be connected to an imaging system, wherein the control handle comprises:
        a body;
        a movement control mechanism disposed at least partially within the body, the movement control mechanism comprising:
            one or more control elements disposed on the body;

a pair of gears rotatably disposed within the body and operably connected to the one or more control elements, the pair of gears including engagement structures thereon; and one or more cables engaged with the pair of gears, the one or more cables extending outwardly from the body and engaged with the imaging tip; and a motion locking mechanism disposed at least partially within the body, the motion locking mechanism comprising:

a pair of brake rods biased into engagement with the engagement structures on the pair of gears; and a release switch selectively engaged with the pair of brake rods to independently position each of the pair of brake rods into or out of engagement with the engagement structures on one of the pair of gears.

14. The interventional medical device of claim 13, wherein the motion locking mechanism includes one or more springs biasing the pair of brake rods.

15. The interventional medical device of claim 13, wherein the pair of brake rods each include a pin extending outwardly from the pair of brake rods and engaged with the release switch.

16. The interventional medical device of claim 15, wherein the release switch includes an engagement flange having multiple notches that receive the pin therein.

17. The interventional medical device of claim 13, wherein the interventional medical device is a transesophageal echocardiography probe.

18. A method for controlling movement of an interventional medical device in an interventional medical procedure, the method comprising the steps of:

providing the interventional medical device comprising:
an insertion tube assembly having an imaging tip at one end; and
a control handle operably connected to the insertion tube opposite the imaging tip and adapted to be connected to an imaging system, wherein the control handle comprises:
a body;
a movement control mechanism disposed at least partially within the body, the movement control mechanism comprising:
one or more control elements disposed on the body;
a pair of gears rotatably disposed within the body and operably connected to the one or more control elements, the pair of gears including engagement structures thereon; and
one or more cables engaged with the pair of gears, the one or more cables extending outwardly from the body and engaged with the imaging tip; and
a motion locking mechanism disposed at least partially within the body, the motion locking mechanism comprising:
a pair of brake rods biased into engagement with the engagement structures on one of the pair of gears; and
a release switch selectively engaged with the pair of brake rods to independently position and hold each of the pair of brake rods into or out of engagement with the engagement structures on one of the pair of gears;
operating the movement control mechanism to move the imaging tip; and
operating the motion locking mechanism to restrict movement of the movement control mechanism in one or more directions.

19. The method of claim 18, wherein the step of operating the motion locking mechanism comprises moving the release switch to overcome the bias on the one or more brake rods to selectively engage the motion locking mechanism with the movement control mechanism.

20. The method of claim 18, wherein the pair of brake rods each include a pin extending outwardly from the pair of brake rods, and wherein the release switch includes an engagement flange having multiple notches that receive the pin therein, and wherein the step of moving the release switch comprises rotating the engagement flange to position the pin within various notches on the engagement flange.

* * * * *